United States Patent [19]

Han

[11] Patent Number: 5,365,625
[45] Date of Patent: Nov. 22, 1994

[54] RING CUTTING AND REMOVING DEVICE

[75] Inventor: Sang I. Han, Northbrook, Ill.

[73] Assignee: Han Medical Designs, Inc., Northbrook, Ill.

[21] Appl. No.: 66,283

[22] Filed: May 20, 1993

[51] Int. Cl.⁵ ............................................. B26B 11/00
[52] U.S. Cl. .......................................... 7/158; 81/302
[58] Field of Search ................ 7/158; 81/302; 29/237; 30/134

[56] References Cited

U.S. PATENT DOCUMENTS

| | | |
|---|---|---|
| 572,644 | 12/1896 | Lemm . |
| 3,287,751 | 11/1966 | Hoffman . |
| 4,395,824 | 8/1983 | Puro . |
| 4,738,017 | 4/1988 | Teramo ............................ 81/302 X |
| 4,790,070 | 12/1988 | Olson . |
| 5,033,195 | 7/1991 | Appelkvist et al. . |

Primary Examiner—James G. Smith
Attorney, Agent, or Firm—Baker & McKenzie

[57] ABSTRACT

A combination ring cutting and removing device is provided for use by medical personnel for cutting and removing rings from injured or swollen fingers. If the finger that carries a ring is badly injured, the swelling of the injured finger often precludes the removal of the ring. The ring must be cut in order to restore circulation to the swollen finger. The combined ring cutting and ring removing device is provided in the form of a plier-type cutting device with a built in means for prying the cut ring apart so the ring can be removed from a swollen finger. The device may also be used for non-medical applications that require a cutting action followed by a prying or separating action.

24 Claims, 5 Drawing Sheets

RING CUTTING AND REMOVING DEVICE

This invention relates generally to an improved tool or device for cuttings rings off of fingers. More specifically, this invention relates generally to a ring cutting and removing device for use by emergency medical technicians, nurses, doctors and others. The device enables a ring disposed on an injured and/or swollen finger to be cut, pried apart and thereafter removed from an injured finger quickly and easily without causing further damage to the finger.

BACKGROUND OF THE INVENTION

The concept of a ring cutting device for cutting and removing a ring from an injured finger is known. These devices are essential equipment in emergency rooms where patients are often treated for injured fingers. For example, if a patient breaks or otherwise seriously injures a fingertip and the finger begins to swell, a ring disposed on the finger will be too narrow to pass over the swollen end of the finger. If the ring remains on the finger, the ring itself could cut off circulation causing further injury to the finger.

The typical device for cutting and removing rings from injured fingers is exemplified by the Beaver Model No. 4100. This device employs a lower gripping arm that slips under the ring and clamps the ring between the arm and a circular saw blade that is turned by hand. After gripping the ring between the gripper arm and the blade, the technician twists the handle thereby rotating the saw blade to eventually cut through the ring. The actual sawing action to sever the ring may take several minutes. Thus, the "saw-type" devices for cutting and removing rings are unsatisfactory because of the time requirements. A patient who is in extreme pain does not appreciate the lengthy procedure required.

Further, the Beaver Model No. 4100 does not include a means for prying the ring apart after the ring is severed. The technician must employ additional equipment in the form of two pairs of pliers or a separate wedging tool to separate the two cut ends of the ring so the ring can be removed from the injured finger.

Thus, there is a need for a ring cutting and removing tool that will cut the ring and pry it apart in one quick and easy procedure. Such a device will be greatly appreciated by patients with painful finger injuries and by busy emergency room personnel who must treat patients at a rapid rate.

SUMMARY OF THE INVENTION

The present invention satisfied the need for a fast and easy ring cutting and removing device for use in emergency medical situations by combining the ring cutting and removing functions in one device. The device is also useful in out-patient clinics, Doctor's offices and is foreseeably useful as a non-medical tool useful for cutting and prying applications. The device of the present invention includes a plier-type ring cutting means that consists of a pair of pivotally mounted jaw/handle combinations. The jaw/handle combinations are in the form of wire cutters. Each jaw carries a sharp cutting blade and the two blades mate when the jaws and handles are in the closed position.

The means for removing the cut ring from the finger is pivotally attached to the means for cutting the ring. The ring removing means provided by two opposingly directed clamps connected to two arms. In the preferred embodiment, an angled joint is disposed between each clamp and each arm. The angled joints are pivotally attached to the handles of the ring cutting means. When the handles and jaws of the ring cutting means are closed, the two opposingly directed clamps are closed. Thus, when the ring is cut, it is also clamped.

In the preferred embodiment, the two opposing clamps are spring biased toward a juxtaposed relationship with the two opposing jaws of the ring cutting means. When the ring is cut, the two clamps grip one end of the ring alongside the two cutting blades and the other end of the ring is disposed on the opposing side of the two cutting blades. After the ring is cut, the operator then pulls the two arms connected to the clamps toward the handles causing the two clamps and the end of the ring gripped therebetween to be pried away from the two cutting blades and the other end of the ring. Essentially, pulling the two arms of the ring removing means toward the handles of the ring cutting means pries the two cut ends of the ring apart so the ring can be removed from the injured finger. In the preferred embodiment, the angled joint disposed between the arms and the clamps acts as a fulcrum for the clamps and pry arms.

In the preferred embodiment, the two clamps are spring biased alongside the two jaws by two springs which extend between the arm of each clamp and its corresponding handle. The springs may be carried by the handle or otherwise accommodated in a slot or aperture disposed in the handle. Further, the springs may be attached to the arms. Thus, the springs push both arms of the ring removing means outward away from the handles and therefore push both clamps of the ring removing means toward or alongside the jaws of the ring cutting means.

When the cut ring is to be pried apart, the user pulls both arms of the ring removing means back toward the handles and each arm and clamp pivot about its angled joint which, in turn, is pivotally attached to each handle of the ring cutting means. In the preferred embodiment, the arms extend rearwardly past the angled joints far enough so as to provide an effective lever for prying a metal ring apart.

Also in the preferred embodiment, the angled joints are pivotally attached to the handles via a yoke and pin combination. Each angled joint is accommodated between two legs of a yoke and a pin extends through both legs and through the angled joint to complete the pivoting connection. The angled joints and yokes are disposed between the clamps and the arms. The springs, which bias the arms away from the handles and the clamps toward the jaws, are attached to the arms between the angled joints and a distal end of each arm. In the preferred embodiment, the two arms, or pry arms, are connected at the distal ends to form a thumb or finger grip that facilitates the prying apart of the ring.

The present invention also lends itself to an improved method of cutting and removing rings from injured fingers in the emergency room conditions. The jaws and clamps are opened or spread apart by opening the handles of the ring cutting means. One jaw and one clamp are slipped underneath the ring. Then, the handles of the ring cutting means are squeezed together thereby causing the cutting blades of the jaws to cut through the ring and assume a mating position. Simultaneously, the clamps of the ring removing means are pushed toward one another thereby tightly clamping the ring between the two inner clamping surfaces of the clamps. The cut ring now includes two cut ends, one end being disposed between the two clamps and the other end being disposed on an opposing side of the jaws and cutting blades.

The user then pushes the distal end of the pry arm of the ring removing means toward the handles of the ring cutting means. As the pry arm moves toward the handles, the clamps with the cut end disposed therebetween pivot outward away from the jaws about an axis defined by the pivotal connection of the clamps to the handles. After the two cut ends of the ring have been sufficiently separated, the ring may now be slid over the swollen injured finger as the effective diameter of the ring has been substantially increased by cutting and separating the two cut ends of the ring. Once the two cut ends of the ring have been separated, circulation has been substantially restored to the injured finger.

An alternative embodiment of the present invention includes two jaw/handle combinations pivotally mounted together. Each jaw also includes a cutting blade for cutting the ring. The ring removing function is provided by two clamps that are pivotally mounted to each other. Each clamp includes a rear extension or leg that is pivotally attached to one handle. Because the clamps themselves are pivotally connected, only one pry bar or prying arm is required to pivot both clamps away from the cutting blades. The alternative embodiment may also be used with the above-described method of cutting and removing rings from injured fingers.

It is therefore an object of the present invention to provide an improved ring cutting and removing device for use by medical technicians, nurses, doctors and others.

It is another object of the present invention to provide an improved ring cutting and removing device that performs both the ring cutting and ring prying or separating functions in one device or apparatus.

Another object of the present invention is to provide an improved tool for cutting and prying, the tool having both medical and non-medical applications.

Other objects, aspects and advantages of the invention will become apparent to those skilled in the art upon reviewing the detailed description, the drawings and the appended claims.

BRIEF DESCRIPTION OF THE DRAWINGS

This invention is illustrated more or less diagrammatically in the accompanying drawings wherein.

DETAILED DESCRIPTION OF THE INVENTION

Like reference numerals will be used to refer to like or similar parts from Figure to Figure in the following description of the drawings.

The dramatic improvement contributed by the present invention is best understood after consideration of how conventional ring cutting devices work and they are used today. Specifically, currently employed ring cutting devices include a lower gripper arm that fits underneath the ring to be cut. The gripper arm is pivotally attached to the handle of the device. The arm is inserted underneath the ring and the handle of the arm is pushed downward thereby gripping the ring and pushing it up against a rotary cutting blade. The user twists a second handle to rotate the rotary cutting blade thereby eventually sawing through the ring.

This process is long and tedious as its takes numerous rotations of the circular blade to cut through a ring. The cutting action alone will take at least several minutes. Second, once the ring is severed, the conventional devices include no means for prying the ring apart to remove it from the injured finger. A separate prying device or devices must be employed to finally remove the ring from the injured finger.

In contrast, the present invention provides a fast and easy ring cutting device that is coupled with a ring removing device. The ring can be cut and removed in one simple and fast procedure.

Figure 1:
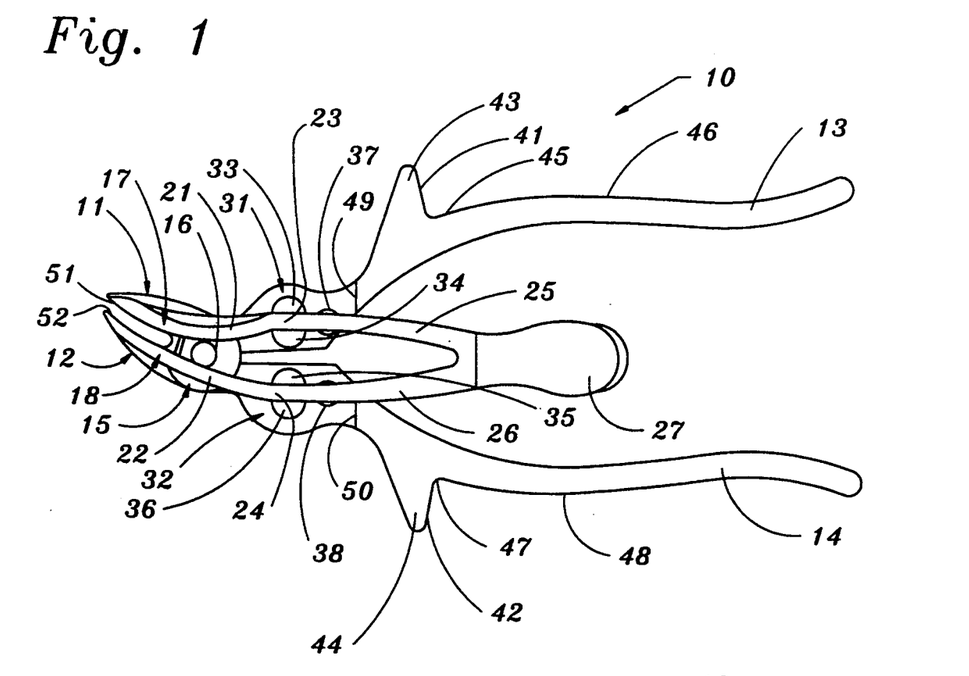
FIG. 1 is a side elevational view of an improved ring cutting and removing device made in accordance with the present invention.

Turning to FIG. 1, a side view of the combination ring cutting and removing device 10 is shown. The device 10 includes two opposingly directed jaws 11, 12. The jaw 12 is attached to the handle 13; the jaw 11 is attached to the handle 14. The handles 13, 14 are pivotally attached together at a central portion 15 by a pin 16 that extends through both handles 13, 14. The combination jaw 12/handle 13 and jaw 11/handle 14 constitute the ring cutting means of the device 10.

The ring removing means of the device 10 is provided by the clamps 17, 18. The clamp 17 extends rearwardly and includes the rear extension or leg 21; the clamp 18 extends rearwardly and includes rear extension or leg 22. The legs 21, 22 are connected to jointed angles 23, 24, respectively. The jointed angles 23, 24, in turn, are connected to rearwardly extending arms 25, 26 respectively. In the preferred embodiment shown in FIG. 1, the pry arms or prying arms 25, 26 are connected at their distal ends to form a thumb or finger grip 27.

Each jointed angle 23, 24 is pivotally attached to its corresponding handle 13, 14 respectively at a yoke member 31, 32 respectively. Referring FIG. 2, the jointed angle 23 of the clamp 17 is disposed within the yoke 31. The yoke 31 is accommodated within the handle 13. Referring back to FIG. 1, the yoke 31 includes an upper leg 33 and a lower leg 34. The jointed angle 23 is accommodated between the two legs 33, 34 and is pivotally held in place via a pivot pin 35 which can be seen in FIG. 2. Again referring to FIG. 2, movement of the arm 25 and/or the grip 27 towards the handle 13 results in the pivotal movement of the clamp 17 away from its corresponding jaw 11. Thus, the clamp 17/arm 25 combination is pivotally attached to the handle 13 at its jointed angle 23 which is disposed within the yoke 31 that is carried by the handle 13.

Returning to FIG. 1, the yoke 32 is disposed within the handle 14 and accommodates the jointed angle 24 that is attached to the jaw 18. The jointed angle 24 is disposed between the upper leg 35 and the lower leg 36 of the yoke 32 and is pivotally held in place with a pivot pin (not shown) that is similar to the pivot pin 35 shown in FIG. 2.

Figure 2:
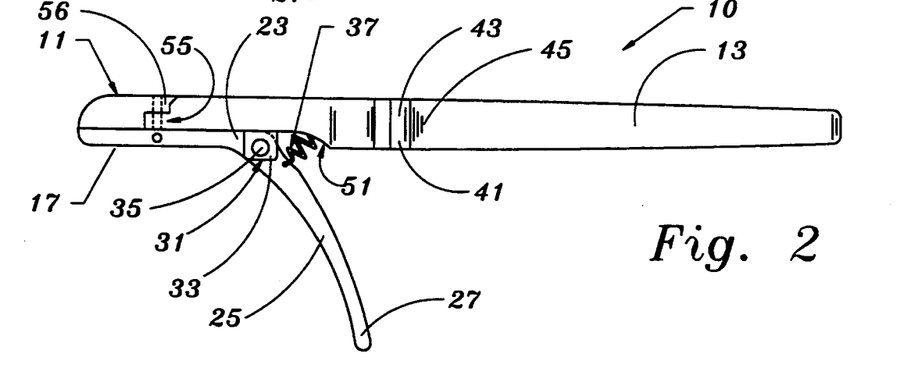
FIG. 2 is a top plan view of the ring cutting and removing device shown in FIG. 1.

Also shown in FIGS. 1 and 2 are the springs 37, 38. As best viewed from FIG. 2, the spring 37 is accommodated between the arm 25 and the handle 13. The spring 37 biases the arm 25 and hence the clamp 17, toward the position illustrated in FIG. 2. Thus, the relaxed position of the clamps 17, 18 is a juxtaposed relationship with the jaws 11, 12 respectively. Similarly, the spring 38 biases the arm 26 outward away from the handle 14 and the spring 38 is also disposed between the handle 14 and the arm 26.

In the preferred embodiment, the springs 37, 38 are accommodated in apertures disposed in the handles 13, 14 respectively. Further, the springs 37, 38 are fixedly attached to the arms 25, 26 respectively by extending a distal coil of each spring 37, 38 through a hole (not shown) disposed in each arm 25, 26. Of course, numerous other means of attachment of the springs 37, 38 to the handles 13, 14 and arms 25, 26 will be apparent to those experienced in the art. In addition to the grip illustrated at 27, the rear surfaces 41, 42 of the upwardly protruding members 43, 44 respectively also serve as finger or thumb grips. Specifically, the index finger of a right-handed operator will engage the junction 45 where the rear surface 41 of the grip 43 meets the upper surface 46 of the handle 13. Similarly, the index finger of a right-handed operator will engage the junction 47 where the rear surface 42 of the member 44 meets the undersurface 48 of the handle 14.

Figure 9:
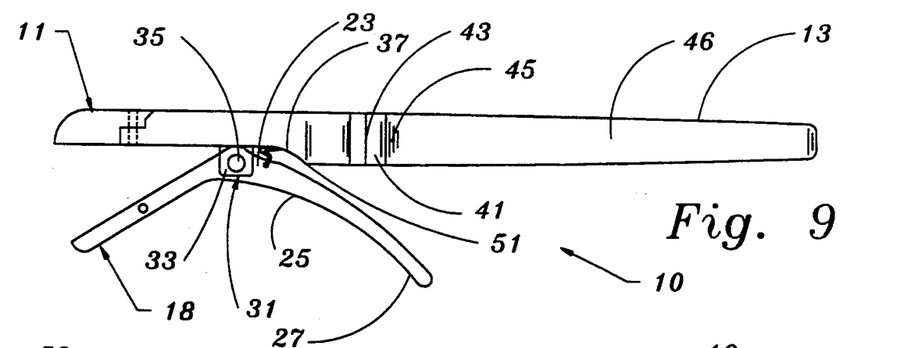
FIG. 9 is a top plan view of the ring cutting and removing device shown in FIG. 1 illustrating the ring removing means as separated or pivoted away from the ring cutting means.

Referring to FIGS. 1 and 2 collectively, the abutments 51, 52 of the handles 13, 14 respectively serve as stops for the arms 25, 26 when the grip 27 is being pulled toward the handles 13, 14 in a prying motion. As best viewed in FIG. 2, the arm 25 will engage the abutment 51 and any additional movement of the arm 25 and grip 27 toward the handle 13 is prevented. This action is also illustrated in FIG. 9 where the arm 25 and grip 27 have been pulled toward the handle 13 and the arm 25 is about to engage the abutment 51. The spring 37 is almost fully compressed.

Also seen in FIG. 1 are the cutting blades 51, 52 carried by the jaws 11, 12 respectively and the gripping surfaces 53, 54 carried by the clamps 17, 18 respectively. These features will be illustrated in more detail in connection with FIGS. 5 through 8 below.

Figure 3:
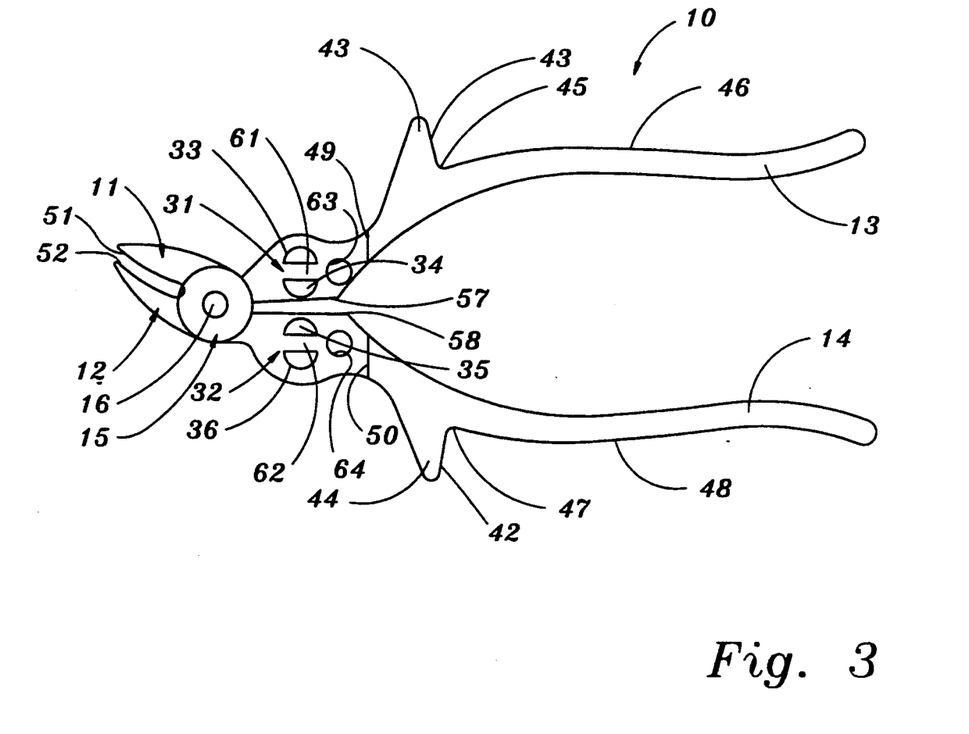
FIG. 3 is a side elevational view of the ring cutting device shown in FIG. 1, the ring removing means being removed therefrom.

Turning to FIG. 3, the ring gripping means or the clamp 17/arm 25 and clamp 18/arm 26 combinations has been removed for a better viewing of the ring cutting means or the jaw 11/arm 14 and jaw 12/arm 13 combinations. It will be noted that the jaw 11 is attached to the handle 14 and the jaw 12 is attached to the handle 13. The handles 13, 14 are pivotally attached to each other at the central portion 15 of the handle 13 and the central portion 56 (see FIG. 2) of the handle 14. The handles 13, 14 pivot about an axis defined by the pivot pin shown at 16 in FIG. 3.

The ring cutting means is in the fully closed position when the cutting blades 51, 52 are in a mating or otherwise abutting engagement. Simultaneously, the undersurfaces 57, 58 of the handles 13, 14 will also be abutting engagement. The yokes 31, 32 are disposed within apertures (not shown) in the handles 13, 14 or the yokes 31, 32 may pass through the handles 13, 14 and be welded or otherwise fixedly attached at opposing sides thereof. The jointed angles 23, 24 (not shown in FIG. 3) are disposed in the slots shown at 61, 62. The slot 61 defines the space between the upper leg 33 and the lower leg 34 of the yoke 31. The slot 62 defines the space between the upper leg 35 and lower leg 36 of the yoke 32. The springs 37, 38 are accommodated within the apertures 63, 64 disposed within the body of the handles 13, 14 respectively.

Figures 4, 5:
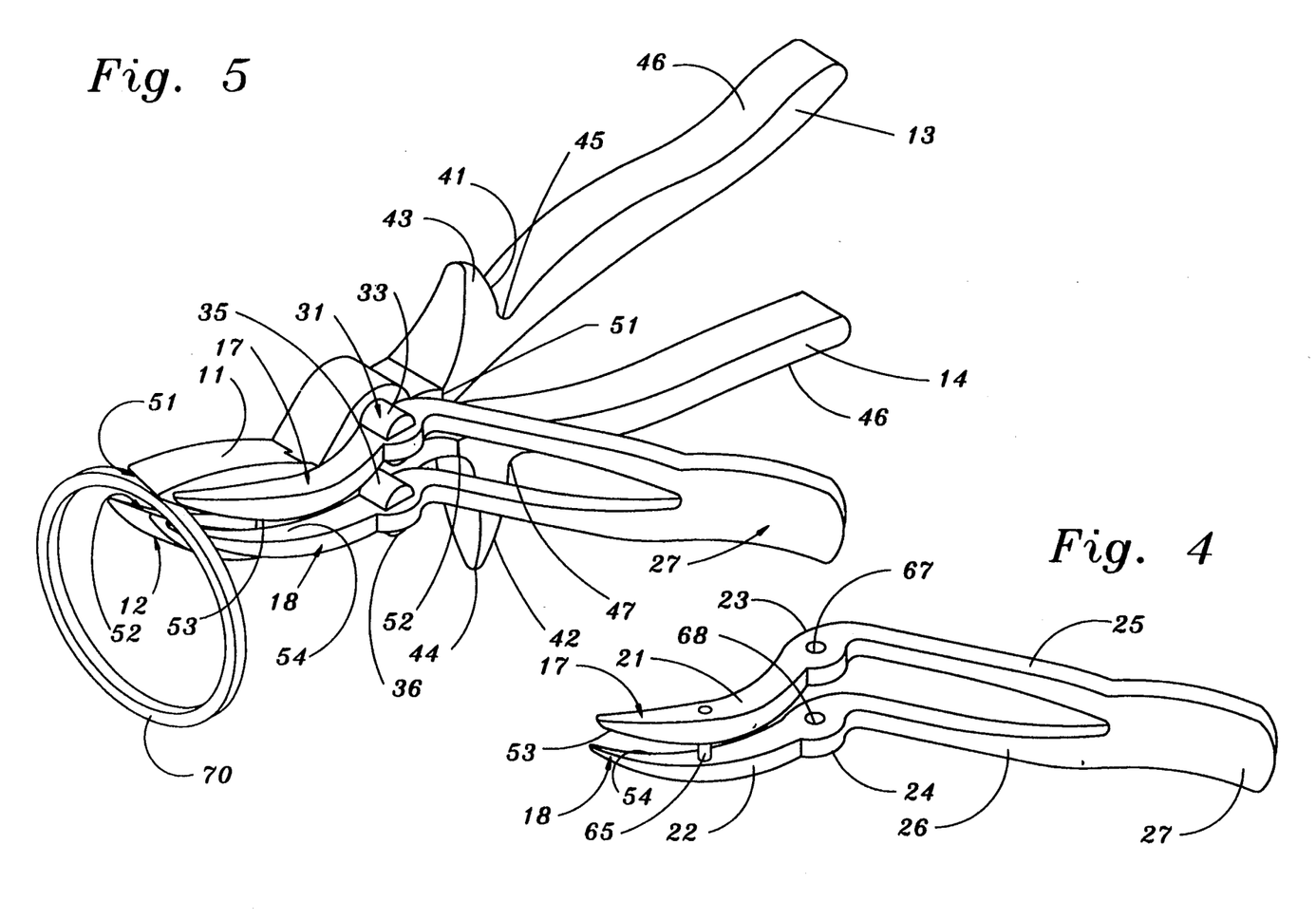
FIG. 4 is a side elevational view of the ring removing means first shown in FIG. 1 as detached from the ring cutting means.
FIG. 5 is a side elevational view of the ring cutting and removing device shown in FIG. 1 in the process of cutting a ring.

Turning to FIG. 4, the preferred embodiment of the ring removing means is shown. The clamp 17 is connected to a rear extension or rear leg 21 which is connected to the jointed angle 23 which is connected to the arm 25. The arm 25 terminates at the grip 27. Similarly, the clamp 18 is connected to the rear extension or rear leg 22 which is connected to the jointed angle 24 which, in turn, is connected to the arm 26 which terminates in the grip 27. In the preferred embodiment, the gripping surfaces 53, 54 are of a rough texture for improved frictional engagement between the clamps 17, 18 and the cut ring as discussed below. A guide bar 65 is also provided in the preferred embodiment to preclude any misalignment of the clamps 17, 18 during the prying or removing action as discussed below. The guide bar 65 is accommodated in the aperture 66 of the rear leg or extension 21 and in a similar aperture (not shown) in the rear leg or extension 22. The apertures 67, 68 in the jointed angles 23, 24 respectively accommodate the pivot pins 35 (see FIG. 2; the pivot pin that extends through yoke 32 is not shown) that extend through the yokes 31, 32 that provide the pivotal attachment of the jointed angles 23, 24 to the handles 13, 14.

The operation of the ring cutting and removing device 10 is illustrated in FIGS. 5 through 9. Turning to FIG. 5, a ring 70 has been grasped between the cutting blades 51, 52 of the jaws 11, 12 as well as between the gripping surfaces 53, 54 of the clamps 17, 18. This position is accomplished by moving the handles 13, 14 toward one another. As seen in FIG. 5 as well as FIG. 1, the clamps 17, 18 are attached to the handles 13, 14 respectively at the yokes 31, 32. Further, the jaws 11, 12 are connected to the handles 14, 13 respectively. Thus, movement of the handles 13, 14 toward one and other also closes the jaws 11, 12 and the clamps 17, 18. As seen in FIG. 5, the ring is firmly engaged and the cutting blades 51, 52 are beginning to cut the ring 70.

Figure 6:
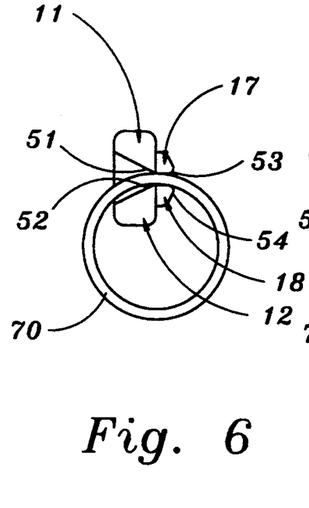
FIG. 6 is a partial front end view of the ring cutting and removing device shown in FIG. 1 as initially engaging a ring.
Figures 7, 8:
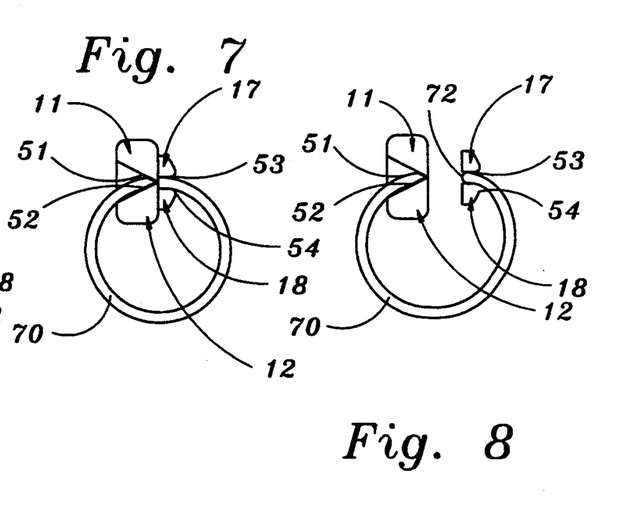
FIG. 7 is a partial front end view of the ring cutting and removing device shown in FIG. 1 as it cuts through a ring.
FIG. 8 is a partial front end view of the ring cutting and removing device shown in FIG. 1 illustrating the ring removing means as separated or pivoted away from the ring cutting means.

Turning to FIG. 6, a front view of the position obtained in FIG. 5 is illustrated. The cutting blades 51, 52 of the jaws 11, 12 respectively are starting to cut the ring 70. The clamps 17, 18 and the clamping surfaces 53, 54 have frictionally engaged the ring 70. In FIG. 7, additional inward pressure is placed by the operator on the handles 13, 14 and the cutting blades 51, 52 mate as they cut through the ring 70. As seen in FIG. 7, the ring is severed and the two cut ends 71, 72 of the ring 70 are ready to be separated. As seen in FIG. 8, the clamps 17, 18 have been pulled away from the jaws 11, 12 by applying inward pressure on the grip 27 (See FIGS. 1, 2 or 5). The clamps 17, 18 have pivoted outward about the jointed angles 23, 24 and the gripping surfaces 53, 54 have pulled the cut end 72 of the ring outward to widen the effective diameter of the ring 70. The cutting blades 51, 52 form a mating engagement after they have cut through the ring 70. Thus, the cut end 71 of the ring is prevented from being pulled outward along with the cut end 72 as the clamps 17, 18 are pulled outward. The cut end 71 is held in place by the cutting blades 51, 52 as seen in FIGS. 7 and 8 and the cut end 72 is pulled outward due to the frictional engagement between the gripping surfaces 53, 54 of the clamps 17, 18. The ring 70 as shown in FIG. 8, is now ready to be removed from an injured finger.

The top view of the ring cutting and removing device 10 as shown in FIG. 8 is illustrated in FIG. 9. The grip 27 has been pulled inward toward the handle 13 (and 14 although not shown in FIG. 9) and the leg 25 is ready to engage the abutment 51 (the leg 26 is also ready to engage the abutment 52 although not shown in FIG. 9). The clamps 17, 18 have been separated from the jaws 11, 12.

An alternative embodiment of the present invention is illustrated in FIGS. 10 through 13. Rather than having the wishbone configuration of the ring removing means as seen in FIGS. 1 through 9, the ring removing means is carried by the ring cutting means. Specifically, the ring cutting and removing device 110 shown in FIG. 10 includes one cutting jaw 111 attached to the handle 112. Similarly, a lower cutting jaw 113 (see FIG. 13) is attached to the handle 114. The upper clamp 115 is connected to the handle 112 as the rear leg or extension 116 of the clamp 115 is accommodated in the slot or aperture 117 disposed in the handle 112. The distal end 118 of the leg 116 is pivotally attached to the distal end 119 of the slot 117 thereby enabling outward pivotal movement of the clamp 115 from the jaw 111 and from the handle 112.

The lower clamp 122 is attached to the upper handle 114 as the rear leg or extension 123 is disposed within the slot 124 disposed within the handle 114. The distal end 125 of the rear leg or extension 123 is pivotally attached to the distal end 126 of the slot 124. Thus, the lower clamp 122 may be pivoted outward from the lower jaw 113 (see FIG. 13) and from the handle 114.

Figure 10:
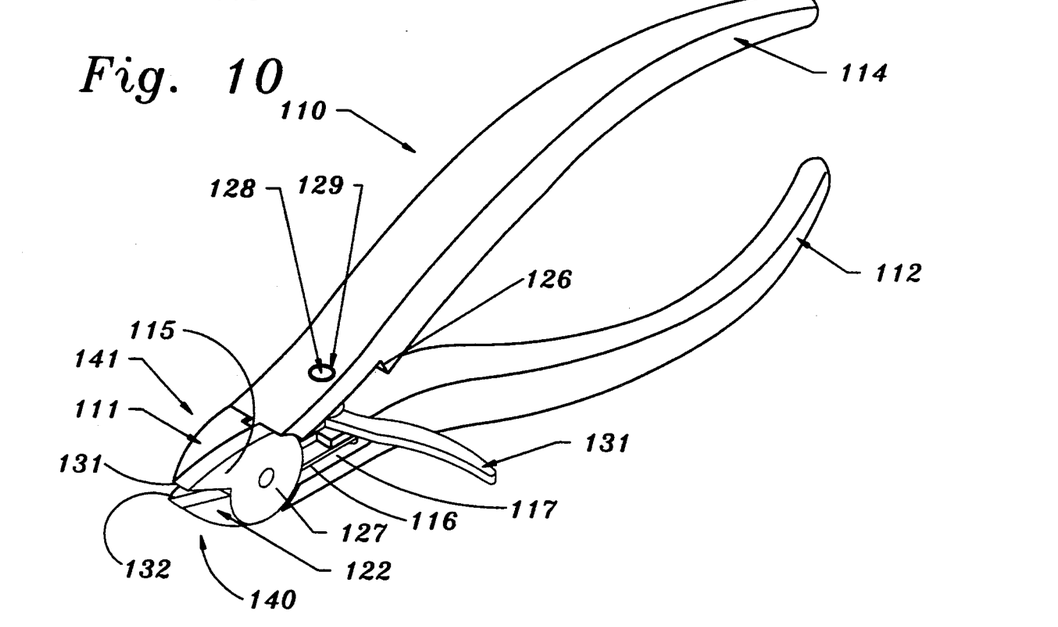
FIG. 10 is a side elevational view of an alternative ring cutting and removing device also made in accordance with the present invention.

The clamps 115 and 122 are pivotally connected to each other at the pivot pin 127. Inward and outward movement of the handles 114, 112 result in the opening and closing of both the jaws 111, 113 and clamps 115, 122. Inward pressure on the pry arm 131 towards the handle 114 results in outward pivotal movement of the clamps 115, 122 for the prying removal of a cut ring. The prying arm 131 and rear leg 123 pivot about the pivot pin 128 which is disposed through the handle 114.

A similar pin is also included for the distal end 118 of the rear leg 116 although not shown in FIG. 10. Again, the clamping surfaces 131, 132 should have a rough texture for improved frictional engagement with a metal ring. The cutting blades 133, 134 (see FIG. 13) should be sharp enough to cut through metal rings.

Figure 11:
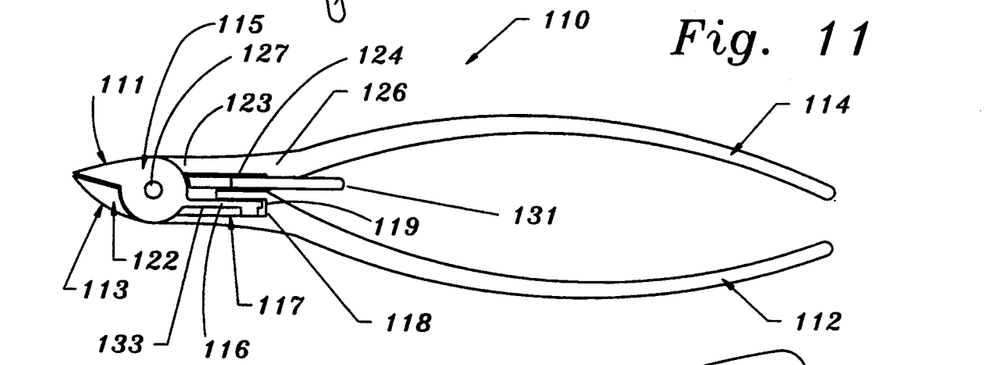
FIG. 11 is a side elevational view of the ring cutting and removing device shown in FIG. 10.

FIG. 11 illustrates the parallel relationship of the pry arm 131 to the slot 124 and the straight relationship between the prying arm 131 and the rear leg 123. Because the rear leg 123 is connected to the lower clamp 122, inward movement of the pry arm 131 pulls the rear leg 123 and the lower clamp 122 outward. Because the clamp 122 is pivotally attached to the upper clamp 115, the outward movement of the lower clamp 122 results in the outward movement of the upper clamp 115. The rear leg 116 of the upper clamp 115 pivots outward as a result of the movement of the upper clamp 115. The wall 133 separates the slots 117, 124 that accommodate the rear legs 123, 116 respectively.

Figure 12:
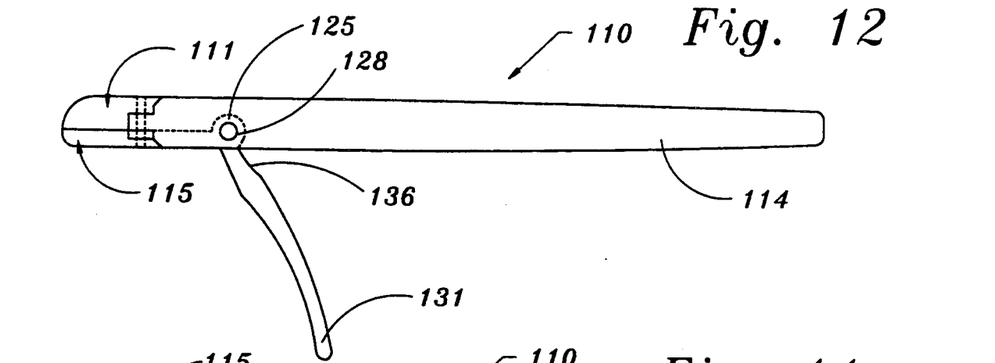
FIG. 12 is a top plan view of the ring cutting and removing device shown in FIG. 10.

Turning to FIG. 12, the ring-cutting position of the device 110 is illustrated. The prying arm 131 is disposed outward from the handles 114, 112 but within reach of an index finger reaching under the handle 112 (see FIG. 10) to grasp the pry arm 131 and pull it inward towards the handle 114. Inward movement of the pry arm 131 is limited by engagement of the surface 136 against the handle 114.

Figures 13, 14:
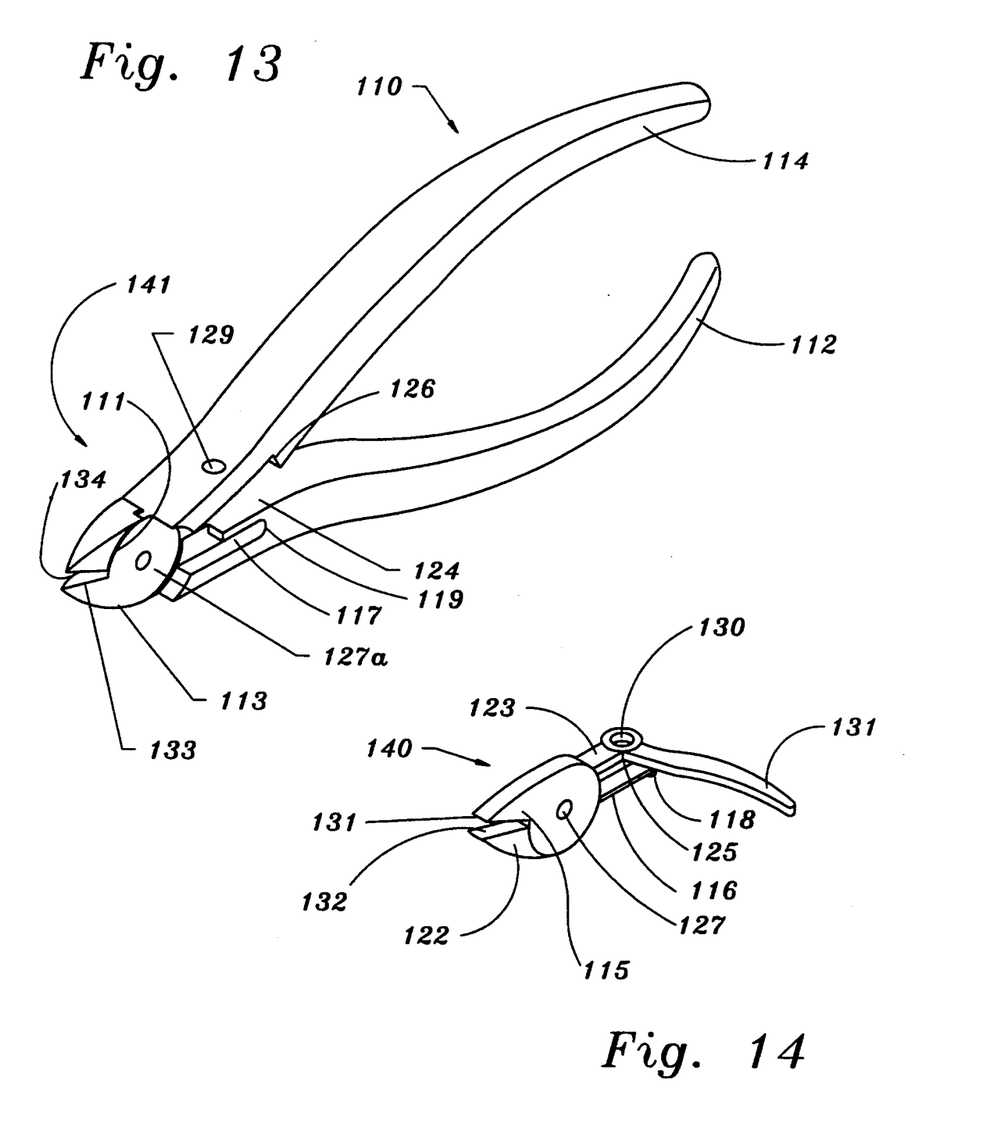
FIG. 13 is a side elevational view of the ring cutting and removing device shown in FIG. 10 with the ring removing means being separated therefrom.
FIG. 14 is a side view of the ring removing means initially shown in FIG. 10 as detached from the ring cutting means.

Turning to FIG. 13, the ring removing means 140 (see FIG. 14) has been removed from the ring cutting means 141. As noted above, the jaw 111 is connected to the handle 112 and the jaw 113 is connected to the handle 114. Sharp cutting blades 134, 133 are provided that mate when the handles 114, 112 are closed. The jaw 113 is pivotally attached to the jaw 111 via the pivot pin 127a. The slot 117 accommodates the rear leg 116 of the upper clamp 115 (see FIG. 10). The slot 124 accommodates the rear leg 123 of the lower jaw 122 (see also FIG. 10). The distal end 125 of the rear leg 123 is pivotally attached to the distal end 126 of the slot 124 with a pin 128 (see FIG. 10) that extends through the pin hole indicated at 129.

Turning to FIG. 14, the ring removing means 140 is illustrated. The clamping surfaces 131, 132 preferably include a rough texture for improved frictional engagement between the surfaces 131, 132 and the ring. The pin 127 pivotally connects the clamps 115, 122 together. The upper clamp 115 is connected to a rear leg or rear extension 116 which includes a distal end 118 that is pivotally connected to the distal end 119 of the slot 117 disposed in the handle 112 (see also FIG. 10). The lower jaw 122 is connected to a rear leg 123 which includes a jointed connection 125 at the distal end thereof which in turn is connected to the pry arm 131. The entire ring removing means 140 pivots about the jointed connection 125 which is pivotally connected to the distal end 126 of the slot 124 in the handle 114 by the pin 128 (see FIG. 10) that extends through the pin hole indicated at 130. The pry arm 131 is curved so as to comfortably accommodate an index finger that extends around the underside of the handle 112 to grasp and pull the arm 131 towards the handle 114 (see also FIG. 10). The operation of the device 110 is analogous to that of the device 10 as illustrated in FIGS. 5-8.

Thus, two embodiments of an improved ring cutting and removing device have been illustrated and described. The improved device provides for a fast cutting operation and fast prying or removing operation. The tedious twisting of the handle to turn a circular saw blade is no longer required and the patient must no longer watch in pain as the user slowly cuts and removes a ring from an injured finger. The present invention will be greatly appreciated by both patients and medical personnel who, under increasing case loads, must treat patients faster and more efficiently than ever before.

Although only two preferred embodiments of the present invention have been illustrated and described, it will at once be apparent to those skilled in the art that variations may be made within the spirit and scope of the invention. Accordingly, it is intended that the scope of the invention be limited solely by the scope of the hereafter appended claims and not by any specific wording in the foregoing description.

I claim:

1. A combination ring cutting and removing device, the device comprising:

means for cutting a ring disposed on a finger including two opposingly directed cutting blades, each blade carried by a jaw, each jaw connected to a handle, the handles being pivotally mounted together, means for separating two ends of a cut ring including two opposingly directed clamps, each clamp being pivotally connected to the means for cutting the ring, the clamps assuming an open position when the jaws assume an open position, the clamps assuming a closed gripping position when the jaws assume a closed cutting position, prying means for moving the clamps from a juxtaposed position with respect to cutting blades to a position disposed laterally outward from the cutting blades, whereby after a ring is cut by the blades to create two cut ends of the ring and the opposing blades engage each other and the opposing clamps engage one cut end of the ring, inward pressure on the prying means results in the opposing clamps separating the two cut ends of the ring for removal of the ring from a finger.

2. The combination ring cutting and removing device of claim 1, wherein the two clamps are pivotally connected together, the prying means includes at least one pry arm connected to at least one clamp.

3. The combination ring cutting and removing device of claim 2, wherein each clamp includes a rear leg attached to a handle of the ring cutting means, each leg is pivotally connected to the handle to which it is attached at a pivot pin that extends through the handle and through the rear leg, the pry arm being connected to at least one rear leg at the pivotal connection of the rear leg to the handle.

4. The combination ring cutting and removing device of claim 1, wherein the prying means includes two pry arms, one pry arm connected to each clamp at a jointed angle, each jointed angle being pivotally attached to a handle.

5. The combination ring cutting and removing device of claim 4, wherein the pry arms are connected together at distal ends thereof to form a thumb grip to facilitate the application of inward pressure on the pry arms to separate the two cut ends of the ring.

6. The combination ring cutting and removing device of claim 5, wherein the device further includes two springs, each spring being disposed between one handle and one pry arm, one end of each spring being carried by the handle, a second end of each spring being attached to the pry arm, the springs biasing the pry arms outward away from the handles of the ring cutting means.

7. A combination ring cutting and removing device, the device comprising:

ring cutting means including a pair of pivotally mounted and opposingly directed jaw/handle combinations, each jaw/handle combination including a handle, a jaw and a central portion for accommodating means for pivotally attaching the jaw/handle combinations together, each jaw carrying a blade, the two blades being opposingly directed to mate and cut a metal ring when a metal ring is disposed therebetween, ring removing means pivotally attached to the ring cutting means, the ring removing means including a pair of opposingly directed clamps, each clamp being pivotally connected to one handle of the ring cutting means, each handle accommodating one clamp, at least one pry arm being attached to one clamp at the pivotal connection of said clamp to its corresponding handle, inward pressure on the pry arm of the ring removing means toward the handles of the ring cutting means resulting in pivotal movement of the clamps arcuately outward away from the blades, whereby after a ring is cut by the blades to create two cut ends of the ring and the opposing blades engage each other and the opposing clamps engage one cut end of the ring, inward pressure on the pry arm results in the clamps separating the two cut ends of the ring for removal of the ring from a finger.

8. The combination ring cutting and removing device of claim 7, wherein the clamps are pivotally connected together, each clamp including a rearwardly extending leg, each rearwardly extending leg being pivotally attached to a handle.

9. The combination ring cutting and removing device of claim 7, wherein the device includes two pry arms, each pry arm being attached to a clamp at the pivotal connection of the clamp to its corresponding handle.

10. The combination ring cutting and removing device of claim 9, wherein the opposingly directed clamps being spring-biased toward a position alongside the opposingly directed blades of the ring cutting means and the prying arms being spring-biased away from the handles of the ring cutting means.

11. The combination ring cutting and removing device of claim 10, wherein the prying arms of the ring removing means are connected together at distal ends thereof to form a thumb grip to facilitate the application of inward pressure on the prying arms to separate the two cut ends of the ring.

12. The combination ring cutting and removing device of claim 11, wherein the clamps include inner clamping surfaces having a rough frictional surface for grasping and pulling the ring.

13. The combination ring cutting and removing device of claim 12,
wherein each handle of the ring cutting means includes a yoke with two legs for accommodating the corresponding angled joint of the ring removing means, each angled joints being contained within the yokes by a pivot pin that extends through both legs of the yoke and through the angled joint to provide the pivotal attachment of each angled joint to the corresponding handle.

14. The combination ring cutting and removing device of claim 13,
wherein the device further includes two springs, each spring being disposed between one handle of the ring cutting means and one arm of the ring removing means,
one end of each spring being carried by the handle, a second end of each spring being attached to the arm,
the springs biasing the prying arms of the ring removing means outward away from the handles of the ring cutting means.

15. A pliers for cutting and removing a ring from a finger, the pliers comprising:
a first jaw attached to a first handle, the first jaw including a first cutting blade,
a second jaw attached to a second handle, the second jaw including a second cutting blade,
the first and second handles being pivotally attached to each other and permitting movement of the first and second cutting blades toward and away from each other,
a first clamp attached to a first arm, the first clamp including a first ring gripping surface,
a second clamp attached to a second arm, the second clamp including a second ring gripping surface,
the first arm being pivotally attached to the first handle, a first spring biasing the first arm outward from the first handle and further biasing the first clamp alongside the second jaw,
the second arm being pivotally attached to the second handle, a second spring biasing the second arm outward from the second handle and further biasing the second clamp alongside the first jaw,
movement of the first and second handles toward each other resulting in movement of the first and second cutting blades toward each other and movement of the first and second clamping surfaces toward each other,
movement of the first and second arms toward the first and second handles resulting in movement of the first and second clamps away from the first and second jaws.

16. The pliers of claim 15,
wherein the first spring is accommodated in a slot in the first handle and the first spring is attached to the first arm,
the second spring is accommodated in a slot in the second handle and the second spring is attached to the second arm.

17. The pliers of claim 16,
wherein the first and second arms are connected together at distal ends thereof to form a thumb grip to facilitate the application of inward pressure on the first and second arms toward the first and second handles to provide movement of the first and second clamps away from the first and second jaws.

18. The pliers of claim 17,
wherein the first handle includes a first yoke with two legs for accommodating the first arm, the first arm being contained within the first yoke by a pivot pin that extends through both legs of the first yoke and through the first arm to provide the pivotal attachment of first arm to the first handle,
the second handle includes a second yoke with two legs for accommodating the second arm, the second arm being contained within the second yoke by a pivot pin that extends through both legs of the second yoke and through the second arm to provide the pivotal attachment of second arm to the second handle.

19. A combination cutting and separating device, the device comprising:
means for cutting including two opposingly directed cutting blades, each blade carried by a jaw, each jaw connected to a handle, the handles being pivotally mounted together,
means for separating including two opposingly directed clamps, each clamp being pivotally connected to the means for cutting,
the clamps assuming an open position when the jaws assume an open position, the clamps assuming a closed gripping position when the jaws assume a closed cutting position,
prying means for moving the clamps from a juxtaposed position with respect to cutting blades to a position disposed laterally outward from the cutting blades,
whereby after a workpiece is cut by the blades to create two cut ends of the workpiece and the opposing blades engage each other and the opposing clamps engage one cut end of the workpiece, inward pressure on the prying means results in the opposing clamps separating the two cut ends of the workpiece.

20. The combination cutting and separating device of claim 19,
wherein the two clamps are pivotally connected together, the prying means includes at least one pry arm connected to at least one clamp.

21. The combination cutting and separating device of claim 20,
wherein each clamp includes a rear leg attached to a handle of the cutting means, each leg is pivotally connected to the handle to which it is attached at a pivot pin that extends through the handle and through the rear leg, the pry arm being connected to at least one rear leg at the pivotal connection of the rear leg to the handle.

22. The combination cutting and separating device of claim 19,
wherein the prying means includes two pry arms, one pry arm connected to each clamp at a jointed angle, each jointed angle being pivotally attached to a handle.

23. The combination cutting and separating device of claim 22,
wherein the pry arms are connected together at distal ends thereof to form a thumb grip to facilitate the application of inward pressure on the pry arms to separate the two cut ends of the workpiece.

24. The combination cutting and separating device of claim 23,
wherein the device further includes two springs, each spring being disposed between one handle and one pry arm,
one end of each spring being carried by the handle, a second end of each spring being attached to the pry arm,
the springs biasing the pry arms outward away from the handles of the cutting means.

* * * * *